(12) United States Patent
Noguchi et al.

(10) Patent No.: US 6,447,759 B2
(45) Date of Patent: Sep. 10, 2002

(54) ULTRAVIOLET ABSORBENT

(75) Inventors: Tamio Noguchi; Yukitaka Watanabe, both of Iwaki (JP)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/839,310

(22) Filed: Apr. 23, 2001

Related U.S. Application Data

(63) Continuation of application No. 09/296,239, filed on Apr. 22, 1999, now abandoned.

(30) Foreign Application Priority Data

Apr. 22, 1998 (JP) ............................................ 98-126616

(51) Int. Cl.[7] .......................... A61K 7/42; C04B 14/00; C04B 14/04; C09C 1/04
(52) U.S. Cl. ......................... 424/59; 106/415; 106/418; 106/425; 106/426; 106/429; 106/482; 424/401
(58) Field of Search .................. 424/401, 59; 106/415, 106/418, 425, 426, 429, 482

(56) References Cited

U.S. PATENT DOCUMENTS

| | | | |
|---|---|---|---|
| 4,331,706 A | * | 5/1982 | Kindrick ...................... 427/74 |
| 5,116,661 A | | 5/1992 | Kimura |
| 5,116,664 A | * | 5/1992 | Kimura et al. .............. 428/216 |
| 5,298,065 A | * | 3/1994 | Hiraoka et al. ............. 106/425 |
| 5,344,488 A | * | 9/1994 | Reynders et al. ........... 106/425 |
| 5,456,749 A | * | 10/1995 | Iwasa et al. ................. 106/417 |
| 5,458,749 A | | 10/1995 | Iwasa et al. |
| 5,951,750 A | * | 9/1999 | Zimmermann et al. ..... 106/417 |

\* cited by examiner

*Primary Examiner*—Jose' G. Dees
*Assistant Examiner*—Marina Lamm
(74) *Attorney, Agent, or Firm*—Millen, White, Zelano & Branigan, P.C.

(57) ABSTRACT

To provide an ultraviolet absorbent having high UV shieldability, especially UV-A shieldability, high transparency and good dispersibility.

An ultraviolet absorbent, which comprises a flaky substrate coated with ultra-fin zinc oxide particles having a mean particle size of not larger than 100 nm, and which is optionally treated with an organic silicone compound; and a method for producing the ultraviolet absorbent, which comprises calcining particles as coated with basic zinc carbonate in the presence of a complex-forming agent.

9 Claims, 1 Drawing Sheet

ULTRAVIOLET ABSORBENT

This is a continuation of application Ser. No. 09/296,239 filed Apr. 22, 1999 now abandoned.

BACKGROUND OF THE INVENTION

The present invention relates to an ultraviolet absorbent with high transparency and good dispersibility, as well as good UV-A shieldability favorable for cosmetic materials. The absorbent of the invention comprises a flaky substrate coated with ultra-fine zinc oxide particles.

Energy of ultraviolet rays triggers off and causes skin aging, deterioration of coating films, deterioration and decomposition of plastics and fading of prints.

The quantity of UV rays falling within a wavelength range of from 290 to 400 nm on the ground accounts for about 6% of the overall quantity of sunlight rays, of which those falling within a short wavelength range of from 290 to 320 nm (hereinafter referred to as UV-B) are about 0.5% and those falling within a long wavelength range of from 320 to 400 nm (hereinafter referred to as UV-A) are about 5.5%. Thus, the quantity of UV-A is large. As having a longer wavelength, UV-A more easily passes through cloud and windowpanes to cause more damage to the skin in daily life, than UV-B. It is said that UV-B scatters on the surface of the skin or is absorbed in the skin to cause sunburn and the like minor inflammations of the surface of the skin, while UV-A penetrates into the dermis below the epidermis of the skin to produce radicals inside the skin tissue, and the radicals thus formed cause photo-aging of the skin to produce wrinkles, to make the skin flabby or to lower the elasticity of the skin, while additionally having some negative influences on cell membranes and genes. Accordingly, in order to protect the skin from ultraviolet rays, it is important not only to shield the skin against the entire region of ultraviolet rays but also to shield it against UV-A especially in the field of cosmetics, and an increasing interest in UV-A shielding is being taken (see the Journal of Cosmetic Technology, 31, No. 1, pp. 14.30, 1997).

Ultraviolet absorbents (UV-shielding agents) are grouped into organic compounds and inorganic compounds. As the ultraviolet absorbents of organic compounds, most typically mentioned are benzotriazole compounds. Because of their UV absorbability, organic ultraviolet absorbents are expected to exhibit quick-acting UV-shieldability, but their use is being reduced as they are problematic in their persistence (activity endurance) and safety. Accordingly, in these days, ultraviolet absorbents (UV-shielding agents) of inorganic compounds free from such problems are being widely noticed.

Most ultraviolet absorbents of inorganic compounds are to exhibit two functions, one being the ultraviolet absorbability of the inorganic compounds themselves and the other being the ability to scatter UV rays (this is referred to as Mie scattering or Rayleigh scattering) to be attained by controlling the particle size of the compound particles. As typical examples of such inorganic compounds, proposed were ultraviolet absorbents comprising metal oxides, such as titanium oxide, zinc oxide, cerium oxide and the like, of which the particle size was controlled (see, for example, Japanese Patent Application Laid-Open (JP-A) Sho-49-450, Hei-5-43682, and Japanese Patent Publication (JP-B) Hei-7-23294).

However, the ultraviolet absorbents comprising such metal oxides are problematic, as so mentioned hereinunder, and are not satisfactory. For example, titanium oxide has an effective absorption range around UV-B, and therefore its particle size must be specifically controlled in order to make it have the shieldability to scatter UV-A. It is said that fine-particle metal oxides having a mean particle size of not larger than 0.1 $\mu$m have the most effective scatterability. However, such fine-particle metal oxides easily aggregate, and therefore require dispersing prior to use. For these reasons, the practical use of the oxides is often difficult. On the other hand, zinc oxide has an effective absorption range around UV-A, and is therefore especially favorable for ultraviolet absorbents for cosmetic materials. However, the compound is problematic in that its chemical stability is poor and that its powder often aggregates. Cerium oxide is also has an effective absorption range around UV-A and is favorable to UV-A shielding. However, as being expensive, the use of the compound is limited.

In order to prevent the particle aggregation, proposed was a technique of applying ultra-fine particles of those metal oxides to particulate substrates (bases), which are larger than the ultra-fine particles, to thereby make the ultra-fine particles adhered by the larger particulate substrates.

For example, JP-B Hei-5-87545 discloses titanium oxide-coated particles; JP-B Hei-3-74641, Hei-9-188611 and JP-A Hei-5-246823 disclose zinc flower-coated or zinc carbonate-coated particles; and JP-A Hei-3-243666 discloses Zinc white-coated, transparent flaky particles.

It is said that the metal oxide-coated materials in those known techniques have transparency for visible rays and have UV-A shieldability. However, the particle size of the flaky substrate to be the base for those is not specifically defined, or, even if defined, the particle size is too large so that the transparency of the materials is poor and the specific surface area of the materials is small. Therefore, in those materials, it is difficult to enlarge the amount of the coating metal oxides which are effective for absorbing and scattering ultraviolet rays. Accordingly, the known materials could hardly exhibit their ultraviolet shieldability. Moreover, nothing is written in the published or laid-open specifications, relating to the particle size and the morphology of the metal oxide particles carried by the substrates on their surfaces; or the particle size of the metal oxide particles defined in those specifications is too large. For these reasons, the known UV absorbents could not satisfy the requirements of good transparency in the range of visible rays and good ultraviolet shieldability, especially that capable of absorbing and scattering UV-A. Specifically, even those of the known UV absorbents which are said to have UV-A shieldability and transparency are still problematic in that their transparency is not satisfactory since the particle size of the flaky substrates is too large, and that their UV-absorbing and scattering ability is not also satisfactory since the particle size of the fine-particle metal oxides adhered on the surface of the substrates is not satisfactorily controlled. Of the known UV absorbents, zinc oxide has an absorption zone near UV-A by itself, and ultra-fine particles of the oxide which are controlled to additionally have UV-A scatterability are favorable to powdery UV-A shielding agents. However, as so mentioned hereinabove, the stability and the dispersibility of the ultra-fine particles is not satisfactory, and therefore the use of the particles is limited. Accordingly, the application of the conventional powdery substances to cosmetic materials, coating compositions, plastics and ink compositions is limited with respect to the method of adding them and to their amount to be added, since the transparency and the dispersibility of the substances is not satisfactory, often resulting in that the substances added or incorporated will have some negative influences on the color tone of the resulting products and that the substances are not easy to handle.

Given that situation, we, the present inventors already proposed an ultraviolet-shielding pigment with good spreadability and adherability especially favorable to cosmetic materials. The pigment comprises a flaky powder coated with zinc oxide and barium sulfate, and has UV-A shieldability, and this is so improved that zinc oxide therein is prevented from aggregating (see JP-A Hei-9-192021).

SUMMARY OF THE INVENTION

Having further studied to improve ultraviolet absorbents of inorganic compounds, the inventors have succeeded in finding an ultraviolet absorbent which has UV-A shieldability and improved transparency and which aggregates little.

Specifically, the present invention provides a novel ultraviolet absorbent, a method for producing it, and a cosmetic material, coating composition, plastic or ink comprising the ultraviolet absorbent, as in the following ① to ⑥.

① An ultraviolet absorbent with high transparency and good dispersibility, which comprises a flaky substrate coated with ultra-fine zinc oxide particles having a mean particle size of not larger than 100 nm. "Mean particle size" is used in the conventional sense, i.e., refers to the long axis of the particle.

② The ultraviolet absorbent of ①, which is prepared by calcining a flaky substrate coated with leafy, basic zinc carbonate particles having a mean major diameter of not larger than 350 nm and a ratio, mean major diameter/mean thickness, of not smaller than 10. In case of the basic zinc carbonate, the particle shape is different from that of zinc oxide particles. The particle shape of zinc oxide is relatively spherical, but the crystal shape of the basic zinc carbonate is like a leaf as described for the precursor in Examples 1–4. The largest (major) length (diameter) in the plane of particle is used to define the particle shape of the basic zinc carbonate.

③ The ultraviolet absorbent of ① or ②, which is prepared by calcining a flaky substrate coated with basic zinc carbonate particles in the presence of a complex-forming agent.

④ The ultraviolet absorbent of any one of ① to ③, wherein the ultra-fine zinc oxide-coated particles are treated with an organic silicone compound to be improved higher dispersibility.

⑤ A method for producing an ultraviolet absorbent with high transparency and good dispersibility, which comprises adding a complex-forming agent to an aqueous suspension of a flaky substrate, then adding thereto an aqueous solution of a zinc salt and an alkali carbonate both at the same time with the resulting suspension being kept at a predetermined pH of not lower than 8.0, or alternatively, adding thereto an aqueous solution of a zinc salt first and then an alkali carbonate followed by further adding thereto an alkaline solution to make the resulting suspension have a pH of not lower than 8, thereby coating the flaky substrate with basic zinc carbonate particles, then filtering it, washing and drying the thus-separated solid, and thereafter calcining it.

① A cosmetic material, coating composition, plastic or ink, which contains the ultraviolet absorbent of any one of ① to ⑤.

The novel ultraviolet absorbent of the invention comprises a flaky substrate coated with ultra-fine zinc oxide particles, in which the coated particles are optionally treated with an organic silicone compound. This is transparent in the region of visible rays, while exhibiting ultraviolet shieldability, especially UV-A shieldability, and is therefore favorably used as an additive to cosmetic materials, coating compositions, plastics and ink compositions because of its such excellent characteristics.

Any and every flaky substrate that is chemically and thermally stable is usable in the ultraviolet absorbent of the invention. For example, employed herein are mica, kaolin, sericite, talc, flaky silica, flaky alumina and synthetic mica.

Of those, preferably selected are flaky substrates with high transparency for use in the field requiring high transparency. In addition, it is desirable to select flaky substrates of which the refractive index is near to that of the materials and media to be combined therewith.

Preferably, the flaky substrate has a mean particle size falling between 0.5 and 10.0 μm, more preferably between 2.0 and 4.0 μm. Having a mean particle size falling within the defined range, the flaky substrate gives ultraviolet-shielding powder with high transparency. The fine-particle, flaky substrate having the defined particle size for use in the invention may be obtained by grinding a substrate material in a grinder, such as a Henschel mixer, an atomizer, a ball mill, a planet mill, a jet mill or the like, in any ordinary dry-grinding or wet-grinding method in which the grinding step may be optionally combined with any classification means of, for example, sieving, pneumatic separation, centrifugation or sedimentation. Substrate particles having a mean particle size of 0.5 μm or smaller will easily aggregate, and therefore require special devices in producing them, resulting in lowering the production efficiency. Even if produced, such fine particles are difficult to handle in transporting and use. In fact, in addition, when used in cosmetic materials and coating compositions, they are difficult to uniformly disperse, as aggregating too much. Moreover, as they have a large specific surface area, the viscosity in media particle size of from 2 to μm is used as the flaky substrate in this invention, the amount of zinc oxide coated on the substrate is preferably from 70 to 130 parts by weight relative to 100 parts by weight of the substrate so as to obtain the intended ultraviolet-shielding powder with high transparency of the invention.

The ultra-fine zinc oxide particles coated on the flaky substrate may be prepared according to the method mentioned below. Specifically, a flaky substrate is suspended in water to give an aqueous suspension, and then a complex-forming agent is added to the suspension, which is thereafter heated at 60° C. or higher. Next, to the suspension containing the complex-forming agent, dropwise added simultaneously are a solution of a zinc salt and a solution of an alkali carbonate with the resulting suspension being kept at a pH of not lower than 8.0, or alternatively, the zinc salt solution is first added thereto and then a predetermined amount of the carbonate solution is added thereto to make the resulting suspension have a pH of not lower than 8. In any of these methods, formed are leafy, ultra-fine, basic zinc carbonate particles having a predetermined particle size on the surface of the flaky substrate. The resulting precursor of the flaky substrate coated with the ultra-fine, basic zinc carbonate particles having a specific particle size and a specific particle morphology is calcined to give the ultraviolet-shielding powder with high transparency of the invention.

To form the basic zinc carbonate particles that constitute the precursor, which is one important element in the method of producing the ultraviolet absorbent of the invention, used is a complex-forming agent. As the complex-forming agent, preferably used is any of citric acid, oxalic acid, ethylenediamine-tetraacetic acid, phthalic acid, maleic acid, tartaric acid, and their alkali metal salts. Of those, especially preferred is trisodium citrate, as it is easy to handle and is economical. As so mentioned hereinabove, the complex-forming agent is effective in controlling the particle size and morphology of the coating, basic zinc carbonate particles. By the use of the complex-forming agent, obtained are the intended basic zinc carbonate particles having the specific particle size and morphology. This is because, the complex-forming agent will act on the basic zinc carbonate particles being precipitated and grown, by which are formed precursor particles having a mean major diameter of not larger than 350 nm and an aspect ratio of not smaller than 10. After having been calcined in the subsequent step, the precursor particles will give ultra-fine zinc oxide particles. The step of precipitating the ultra-fine, basic zinc carbonate particles on the surface of the, flaky substrate is important for obtaining the ultraviolet-shielding powder with high transparency of the invention.

The amount of the complex-forming agent to e used in the invention varies, depending on the type of the agent, but is preferably not smaller than 0.005 mols per mol of the coating zinc salt. If the amount is smaller than that, the particle size of the ultra-fine, basic zinc carbonate particles to be formed may be unfavorably too large. The uppermost limit of the amount is not specifically defined. In general, however, the amount may be from 0.01 to 0.1 mols. A larger amount of the agent than 0.1 mols will be meaningless to reduce the particle size of the ultra-fine, basic zinc carbonate particles to be obtained.

The zinc salt to be used in this step may be any and every water-soluble, inorganic or organic one, which includes, for example, zinc chloride, zinc bromide, zinc iodide, zinc sulfate, zinc nitrate, zinc phosphate, zinc acetate, and zinc oxalate. The amount of the zinc salt to be used is preferably from 30 to 250 parts by weight, in terms of zinc oxide, relative to 100 parts by weight of the flaky substrate. The amount may be suitably determined, depending on the particle size of the flaky substrate. Naturally, a flaky substrate having a small particle size shall have a large specific surface area, and therefore can be coated with a large amount of the zinc oxide. However, in the invention, if the amount of the zinc oxide is smaller than 30 parts by weight, the final product obtained could not exhibit good ultraviolet shieldability, because of not enough amount of Zinc oxide particles coated on the flaky substrate. on the contrary, if the amount is larger than 250 parts by weight, the surface-coated particles will aggregate through their contact and adhesion each other, resulting in that the zinc oxide particles coated on the substrate may not have the intended mean particle size of not larger than 100 nm, most preferably not larger than 50 nm.

The alkali metal carbonate compound to be used in this step may include, for example, potassium carbonate, sodium carbonate and ammonium carbonate. However, ammonium carbonate is not preferred herein in view of regulation of nitrogen dissolved water discharge.

Where the carbonate is added to the substrate suspension simultaneously with the zinc salt solution, the two are added to the suspension while the pH of the resulting suspension is kept to be a predetermined value. In this case, the pH of the suspension is preferably not lower than 8, preferably not lower than 8.5, for the precipitation of the intended basic zinc carbonate therein. Where the zinc salt is first added and then the carbonate is added, the amount of the latter is preferably controlled that the final pH of the resulting suspension is not lower than 8.0.

In the invention, any of those above methods is employable. However, the former is preferred to the latter, in view of the easiness in controlling the particle size of the particles to be formed therein. According to any of those above methods, the intended basic zinc carbonate is formed, and the surface of the flaky substrate is coated with fine particles of the carbonate precipitated thereon.

The mechanism of forming the fine-particle, basic zinc carbonate is not always clarified. However, it is believed that, as so mentioned hereinabove, the complex-forming agent and the alkali carbonate existing in the system will control the nucleation speed and the growth of the particles being formed therein, whereby the intended, ultra-fine, basic zinc carbonate particles may be formed on the surface of the substrate. The alkali metal carbonate is, in addition to the complex-forming agent noted above, another, component for controlling the particle size and morphology of the particles to be formed on the surface of the substrate. If only a different basic substance such as an alkali hydroxide or ammonia is used herein, in place of the carbonate, to form zinc hydroxide, and if the substrate is coated with the thus-formed zinc hydroxide, the intended, ultra-fine particles as defined may not be formed on the substrate. Even if the substrate coated with such zinc hydroxide particles is calcined, the resulting zinc oxide-coated powder has poor transparency, though having ultraviolet shieldability in some degree.

In the method of the invention, the suspension is, after the zinc salt solution and the carbonate solution are added thereto, stirred for about 30 minutes, and thereafter the solid is separated from the suspension through filtration. The filtration is combined with washing the solid with water. Alternatively, for the washing, employable is also that, the solid residue obtained through the filtration may be again dispersed in water, and the aqueous dispersion may be again filtered, and these process are repeated. After having been washed, the solid residue is dried at about 110° C. As a result of analysis through powdery X-ray diffractometry, it was confirmed that, in the dried powder, the coating particles were of basic zinc carbonate. (The basic zinc carbonate referred to herein is meant to include "zinc compounded with $CO_3$ and OH in a composite state" and its hydrates.) SEM observation of the powder verified that the coating particles had a mean major diameter of not larger than 350 nm and were leafy to have an aspect ratio, mean major diameter/mean thickness, of not smaller than 10. The flaky substrate thus coated with such basic zinc carbonate particles is a precursor, which is, after calcined, to be the intended, flaky substrate coated with ultra-fine zinc oxide particles of the invention.

The aspect ratio of the coating particles may be suitably changed, by varying the complex-forming agent to be used and the amount thereof relative to the zinc salt.

The dried powder is calcined at a temperature falling between about 300 and 900° C., preferably about 500 and 900° C. Through SEM observation, the calcined powder was found to be such that the coating particles therein have a mean particle size of not larger than 100 nm. It is believed that, as a result of calcining the dried powder, the carbonate moiety in the coating, basic zinc carbonate particles is pyrolyzed to release carbon dioxide therefrom so that the coating particles become finer. If the powder is calcined at a temperature lower than 300° C., the coating particles could not be oxidized satisfactorily. However, if the powder is calcined at a temperature higher than 900° C., such high-temperature calcining will induce solid-phase reaction of the coated, ultra-fine zinc oxide particles formed, resulting in that the coated particles have a large particle size. Through powdery x-ray diffractometry of the calcined powder, the presence of zinc oxide in the powder was confirmed. The thus-obtained powder can be used directly without further treatment. However, in order to enhance its ability, desirably, the powder is further pulverized and dispersed.

The thus-obtained powder may be treated with an organic silicone compound, such as an alkylhydrogen-polysiloxane, to coat the particles with the compound. This is to prevent the aggregation of the coated substrate and to enhance the dispersibility of the coated substrate, thereby facilitating the production of the cosmetic material, the coating composition, the plastic and the ink of the invention that comprises the coated substrate. To coat the coated substrate with such an organic silicone compound, for example, employable is any of a dry method of directly mixing the silicone compound with the powder, or a wet method comprising suspending the powder in water with silicone compound, and then dewatering and drying it. In the dry process, the two may be directly mixed, or alternatively, the two may be mixed along with any other diluting solvent and the solvent used may be removed from the mixture through vaporization. In the wet process, when an alkylhydrogen-polysiloxane having high solubility in water is used, special attention shall be paid in order to prevent the silicone from flowing out without adhering onto the surfaces of the particles. However, silicone compounds not completely dissolving in water are unfavorable, since they could not naturally reach the surfaces of the powder coated substrate and could not adhere uniformly onto the surfaces of the coated substrate. In the wet process, it is necessary that the alkylhydrogen-polysiloxane to be used is suitably selected in consideration of the solubility of the compound in the media, and the property relative to water of the compound as to whether or not the compound is hydrophilic or hydrophobic.

Alkylhydrogen-polysiloxanes usable herein include, for example, methylhydrogen-polysiloxane, ethylhydrogen-polysiloxane, propylethylhydrogen-polysiloxane, butylhydrogen-polysiloxane, pentylhydrogen-polysiloxane, and hexylhydrogen-polysiloxane. Those alkylhydrogen-polysiloxanes are to be suitably selected in consideration of their polarity in cosmetic materials, coating compositions, plastics and ink compositions and also of the related legal controls on their use. For example, in cosmetic materials, methylhydrogen-polysiloxane is favorably used in view of the legal controls thereon. The product obtained in the wet process is filtered to separate the solid residue from the suspension, and the thus separated solid residue is then dried. The powder thus obtained in any of those wet and dry process is finally heated to thereby bake the alkylhydrogen-polysiloxane onto the surfaces of the powdery particles.

In general, the powder is dewatered and heated at a temperature not lower than 100° C., preferably at about 130° C., in consideration of the producibility of the powder according to this invention. In the invention, the amount of the alkylhydrogen-polysiloxane to be used may be not smaller than 0.5 parts by weight relative to 100 parts by weight of the powder to be treated therewith. Though not specifically defining the uppermost limit of the amount of the compound to be used the amount thereof may be suitably determined in accordance with the economical aspect and of the physical property of the compound. Normally 1~5 weight parts are employable.

The powder thus obtained may be directly the ultraviolet shielding powder with high transparency of the invention. If desired, the powder may be pulverized using, for example, a ball mill, an atomizer, a planet mill or the like and then it is obtainable, to be an ultraviolet shielding powder having higher dispersibility with no aggregation and having higher transparency.

Temperatures are set forth uncorrected in degrees Celsius; and, unless otherwise indicated, all parts and percentages are by weight.

The entire disclosure of all applications, patents and publications, cited above and below, and of corresponding Japanese application No. 98-12661G, filed Apr. 22, 1998 is hereby incorporated by reference.

EXAMPLES

Example 1

50 g of mica having a mean particle size of 2.u $\mu$m and a specific surface area of 15.01 $m^2/g$ was added to 1 liter of water to prepare an aqueous suspension. This suspension was heated at 75° C., to which was added 9.03 g (0.05 mols relative to zinc) of a complex-forming agent of trisodium citrate dihydrate, and stirred. Apart from this, 176.7 g of zinc sulfate 7-hydrate was used to prepare an aqueous 20 wt. % solution of the salt. Also prepared was an aqueous 30 wt. % solution of potassium carbonate. The aqueous zinc sulfate solution was added to the suspension at a rate of 3 ml/min, along with the aqueous potassium carbonate solution with which the pH of the resulting suspension was kept to be 8.5. After the addition, the suspension was stirred for about 10 minutes, then filtered and washed to obtain a solid residue. The solid residue was dried at about 110° C. for 8 hours, and then calcined at 700° C. The aggregates in the resulting powder were pulverized, using a blender. In the final powder to be obtained herein, the amount of zinc oxide was controlled to be 100 parts by weight relative to 100 parts by weight of mica. Through its powdery X-ray diffractometry, the dried precursor powder was found to have basic zinc carbonate therein. Through the SEM picture of the powder, it was found that the coating particles existing in the powder had a mean major diameter of 20 nm and were leafy to have an aspect ration (mean major diameter/mean thickness) of 11.8. In the calcined powder, the coating, ultra-fine zinc oxide particles had a mean particle size of 40 nm. The powder obtained herein had good dispersibility and high transparency.

Example 2

The same process as in Example 1 was repeated herein, except that the complex-forming agent was not used. In the final powder obtained herein, the amount of zinc oxide was 100 parts by weight relative to 100 parts by weight of mica. Through the SEM picture of the dried precursor powder, it was found that the coating particles existing in the powder had a mean major diameter of 250 nm and were leafy to have an aspect ratio (mean major diameter/mean thickness) of 12.5. In the calcined powder, it was found that the, ultra-fine zinc oxide coated substrate were partly aggregated. The ultra-fine particles of zinc oxide had a mean particle size of 50 nm except for aggregated particles of Zinc oxide thereon.

Example 3

150 g of mica having a mean particle size of 5.9 $\mu$m and a specific surface area of 7.7 $m^2/g$ was added to 1.5 liters of water to prepare an aqueous suspension.

This suspension was heated at 75° C., to which was added 27.1 g (0.05 mols relative to zinc) of a complex-forming agent of trisodium citrate dihydrate, and stirred. Apart from this, 530 g of zinc sulfate 7-hydrate was used to prepare an aqueous 30 wt. % solution of the salt. Also prepared was an aqueous 30 wt. % solution of potassium carbonate. The aqueous zinc sulfate solution was added to the suspension at a rate of 5 ml/min, along with the aqueous potassium carbonate solution with which the pH of the resulting suspension was kept to be 8.5. After the addition, the suspension was stirred for about 30 minutes, then filtered and washed to obtain a solid residue. The solid residue was dried at about 110° C. for 8 hours, and then calcined at 700° C. In the final powder to be obtained herein, the amount of zinc oxide was controlled to be 100 parts by weight relative to 100 parts by weight of mica. Through its powdery X-ray diffractometry, the dried precursor powder was found to have basic zinc carbonate therein. Through the SEM picture of the powder, it was found that the coated particles existing in the powder had a mean major diameter of 330 nm and were leafy to have an aspect ratio (mean major diameter/mean thickness) of 13.2. In the calcined powder, the coated, ultra-fine zinc oxide particles had a mean particle size of 40 nm.

100 g of mica having a mean particle size of 5.9 $\mu$m and a specific surface area of 7.7 $m^2$/g was added to 2 liters of water to prepare an aqueous suspension.

This suspension was heated at 75° C., to which was added 9.33 g (0.1 mols relative to zinc) of a complex-forming agent of succinic acid, and stirred. Apart from this, 151.6 g of zinc sulfate 7-hydrate was used to prepare an aqueous 20 wt. % solution of the salt. Also prepared was an aqueous 30 wt. % solution of potassium carbonate. The aqueous zinc sulfate solution was added to the suspension at a rate of 3.5 ml/min, along with the aqueous potassium carbonate solution with which the pH of the resulting suspension was kept to be 8.5. After the addition, the suspension was stirred for about 10 minutes, then filtered and washed to obtain a solid residue. The solid residue was dried at about 110° C. for 8 hours, and then calcined at 700° C. In the final powder to be obtained herein, the amount of zinc oxide was controlled to be 43 parts by weight relative to 100 parts by weight of mica. Through its powdery X-ray diffractometry, the dried precursor powder was found to have basic zinc carbonate therein. Through the SEM picture of the powder, it was found that the coated particles existing in the powder had a mean major diameter of 330 nm and an aspect ratio (mean major diameter/mean thickness) of 13.2. In the calcined powder, the coated, ultra-fine zinc oxide particles had a mean particle size of 40 nm.

Example 5

1.5 kg of the powder obtained in the same manner as in Example 1 was put into a 20-liter Henschel mixer, and stirred at 2800 rpm for 18 minutes. Next, 30 g of methylhydrogen-polysiloxane was added thereto and further stirred at 350 rpm for 3minutes. The resulting mixture was heated at 130° C.,while being further stirred therein at 2800rpm for 18 minutes. Next, this was cooled for about 6 minutes while being stirred at 2800 rpm, and then further cooled to about 50° C. at 350 rpm. Thus was obtained the powder of the invention. The powder had better dispersibility and higher transparency.

Example 6

50 g of the powder obtained in the same manner as in Example 1 was suspended in 1 liter of water, and heated at 75° C. To this was added a 10% solution of hydrochloric acid, with which the pH of the suspension was controlled to be 7, and the resulting suspension was stirred for about 10 minutes. Next, 1 g of methylhydrogen-polysiloxane was added to the suspension with stirring, and further stirred for about 30 minutes. Then, the suspension was filtered and washed, and the solid residue obtained was dried and heated at 130° C. The aggregates existing in the resulting powder were pulverized, using a blender, to obtain the intended powder of the invention. The powder had better dispersibility and higher transparency.

Comparative Example 1

150 g of fine-powdery muscovite having a particle size of from 1 to 15 $\mu$m was suspended in 1.5 liters of water, and heated at about 80° C., to which was added 50.7 g of barium hydroxide with stirring. Next, an aqueous solution of 10 wt. % sulfuric acid was dropwise added to the resulting suspension at a rate of 2 ml/min, with stirring, with which the pH of the suspension was controlled to be finally 3. After the addition, the suspension was stirred for about 10 minutes, to which was added 662.5 g of zinc sulfate, and further stirred for about 10 minutes. Then, an aqueous 32 wt. % solution of sodium hydroxide was dropwise added to this at a rate of 5 ml/min, with which the final pH of the suspension was controlled to be 8.5. This suspension was filtered to separate the solid residue therefrom, and the solid residue was washed, then dried at about 105° C. for 15 hours, and thereafter calcined at 700° C. In that manner, obtained was an ultraviolet-shielding pigment in which 100 parts by weight of powdery muscovite was coated with 25 parts by weight of barium sulfate particles and 125 parts by weight of zinc oxide particles. The SEM observation of the pigment verified that the barium sulfate particles existing therein had a mean particle size of about 0.3 $\mu$m and that the needle-like zinc oxide particles also existing therein had a mean major diameter of 0.2 $\mu$m.

Comparative Example 2

The same process as in Example 1 was repeated, except that sodium hydroxide was used in place of potassium carbonate. In the final powder obtained herein, the amount of zinc oxide was 100 parts by weight relative to 100 parts by weight of mica. Through the SEM picture of the dried precursor powder, it was found that the coated particles existing in the powder had a mean major diameter of 170 nm and an aspect ratio (mean major diameter/mean thickness) of 3.4. In the calcined powder, the coating, ultra-fine zinc oxide particles had a mean particle size of 170 nm.

Evaluation of Ultraviolet Shieldability and Transparency of Powder Samples

The powder samples obtained in Examples 1 to 6 and Comparative Examples 1 and 2 were separately dispersed in a PVC-type medium by hand (without using any mechanical means of Hoover muller, three-roll mixer and the like) to prepare 20 wt. % dispersions. Each dispersion was applied onto sheet glass, using an applicator having a thickness of 120 $\mu$m, to form thereon a film. After having been dried, the film was subjected to spectrophotometry, using Hitachi's 228 Model spectrophotometer, to measure its transmittance within a wavelength range of from 200 and 900 nm. The transmittance at 300 nm indicates the data for UV-B; that at 370 nm for UV-A; and that at 550 nm for visible rays. In addition, the absorbance for UV-A and UV-B was also measured. FIG. 1 shows the transmittance of the samples of Example 1, Comparative Examples 1 and 2; and Table 1 shows the data of the transmittance and the absorbance of the samples tested herein for ultraviolet rays (300 nm for UV-B and 370 nm for UV-A) and for visible rays (550 nm).

TABLE 1

Transmittance in ultraviolet and visible ray range, and Absorbance in ultraviolet range

| Sample | Transmittance (%) UV-B 300 nm | UV-A 370 nm | Visible Rays 550 nm | Absorbance UV-B 300 nm | UV-A 370 nm |
|---|---|---|---|---|---|
| Example 1 | 1.23 | 1.80 | 56.11 | 1.91 | 1.75 |
| Example 2 | 1.47 | 1.48 | 52.31 | 1.84 | 1.83 |
| Example 3 | 8.65 | 7.93 | 53.18 | 1.07 | 1.10 |
| Example 4 | 7.69 | 10.14 | 71.92 | 1.12 | 1.00 |
| Example 5 | 0.87 | 0.98 | 62.46 | 2.06 | 2.01 |
| Example 6 | 1.30 | 1.90 | 67.03 | 1.89 | 1.72 |
| Comparative Example 1 | 6.97 | 5.08 | 26.30 | 1.16 | 1.29 |
| Comparative Example 2 | 1.92 | 0.99 | 35.17 | 1.72 | 2.01 |

The samples of Examples 1 to 6 were found to have higher transmittance in the visible ray range while having lower transmittance in the ultraviolet range, than those of Comparative Examples of those, the characteristics of the samples of Examples 5 and 6 that had been coated with a hydrogen-polysiloxane and had been pulverized were much better to meet the object of the invention.

Application Examples

Using the ultraviolet-shielding powder samples obtained in Examples 1 to 6, prepared were cosmetic materials (A: compact powder, and B: foundation) each having the composition mentioned below.

A: Formulation of Compact Powder:

Composition:

| | |
|---|---|
| UV-shielding pigment obtained in any of Examples 1 to 6 | 25 wt. pts. |
| Coloring pigment | 5 wt. pts. |
| Lanolin | 3 wt. pts. |
| Isopropyl myristate | balance |
| Magnesium stearate | 2 wt. pts. |
| Talc | 50 wt. pts. |

B: Formulation of Foundation:

Composition:

| | |
|---|---|
| Talc (JA-46R, manufactured by Asada Talc) | 38 wt. pts. |
| Mica (mean particle size: about 8 $\mu$m) | 10 wt. pts. |
| Magnesium stearate | 3 wt. pts. |
| Nylon powder 12 | 8 wt. pts. |
| Yellow iron oxide | 1.9 wt. pts. |
| Red iron oxide | 0.8 wt. pts. |
| Titanium oxide | 1.0 wt. pts. |
| Sample obtained in any of Examples 1 to 6 | 30 wt. pts. |
| Mineral oil (70) | 3.9 wt. pts. |
| (Caprylic acid/capric acid) triglyceride | 3.3 wt. pts. |
| Butylparaben | 0.1 wt. pts. |

2. Use in Coating Compositions

Using the ultraviolet-shielding powder samples obtained in Examples 1 to 6, prepared were coating compositions in the manner mentioned below.

Coating Composition (for Automobiles)
Composition A (Acrylic Melamine Resin):

| | |
|---|---|
| Acrydic 47-712 | 70 wt. pts. |
| Superbeccamine G821-60 | 30 wt. pts. |

Composition B:

| | |
|---|---|
| UV-shielding powder obtained in any of Examples 1 to 6 | 10 wt. pts. |
| Pearly pigment | 10 wt. pts. |

Composition C (Thinner for Acrylic Melamine Resin):

| | |
|---|---|
| Ethyl acetate | 50 wt. pts. |
| Toluene | 30 wt. pts. |
| N-butanol | 10 wt. pts. |
| Sorbesso #150 | 40 wt. pts. |

20 parts by weight of the composition B was mixed with 100 parts by weight of the composition A, which was then diluted with the composition C to have a viscosity suitable for spray coating (12 to 15 seconds as measured with Ford Cup #4). The resulting mixture was sprayed over a substrate to form a base coat layer thereon.

3. Use as Filler in Plastics

Using the ultraviolet-shielding powder samples obtained in Examples 1 to 6, prepared were plastics in the manner mentioned below.

Composition (Plastic Composition):

| | |
|---|---|
| High-density polyethylene resin (pellets) | 100 wt. pts. |
| UV-shielding powder obtained in any of Examples 1 to 6 | 1 wt. pt. |
| Magnesium stearate | 0.1 wt. pts. |
| Zinc stearate | 0.1 wt. pts. |

The pellets were dry-blended with the additives in the ratio noted above, and molded through injection molding into plastic moldings.

4. Use in Printing Ink

Composition:

| | |
|---|---|
| CCST medium (nitrocellulose resin, manufactured by Toyo Ink Co.) | 10 wt. pts. |
| UV-shielding powder obtained in any of Examples 1 to 6 | 8 wt. pts. |

A solvent, NC 102 (manufactured by Toyo Ink Co.) was added to the ink composition noted above to prepare printing ink having a viscosity of 20 seconds as measured with Zahn Cup No. 3.

As is obvious from Table 1, the ultraviolet absorbent of the present invention has not only UV-shieldability but also high transparency in the visible ray range. Therefore, when it is incorporated into practicable cosmetic materials, coating compositions, plastics and ink compositions, it has little influence on the color change in those products. Accordingly, the amount of the ultraviolet absorbent capable of being added to those products may be increased, whereby the UV-shieldability of the. products can be increased.

Figure 1:
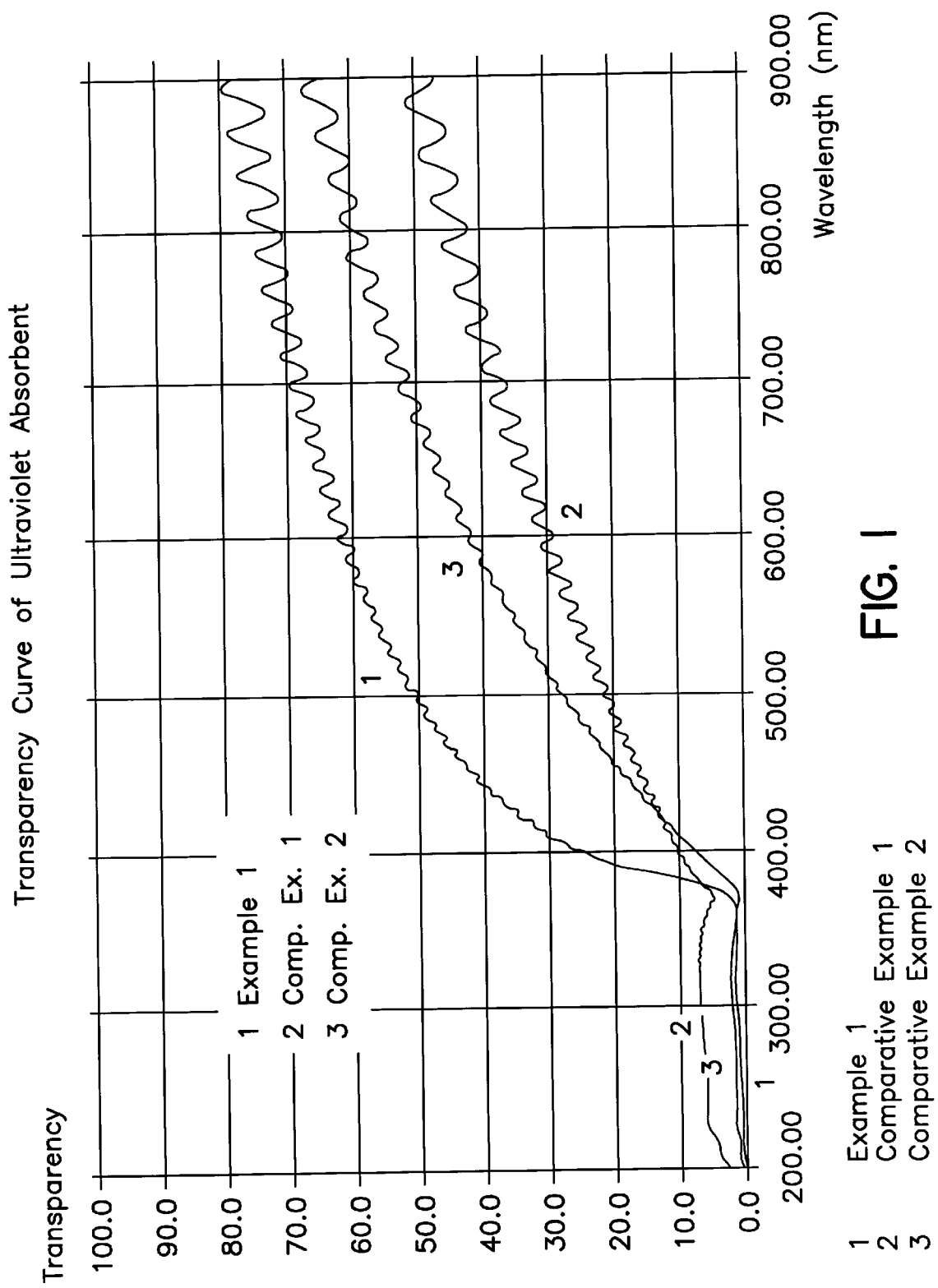
[FIG. 1] This shows the transmittance of the ultraviolet absorbent samples obtained in Example 1 and Comparative Examples 1 and 2, in a wavelength range of from 200 nm to 900 nm.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A ultraviolet absorbent comprising a flaky substrate coated with ultra-fine zinc oxide particles having a mean particle size less than 50 nm, wherein said absorbent is prepared by:

suspending said substrate to form a suspension;

adding a complex forming agent to said suspension;

adding at least one zinc salt and at least one alkali carbonate to the suspension to thereby form basic zinc carbonate particles on the surface of said flaky substrate;

calcining said flaky substrate at 300–900° C.; and wherein said ultraviolet absorbent has high transparency in the visible range, UV-A shieldability and a reduced zinc oxide aggregation tendency.

2. The ultraviolet absorbent according to claim 1, wherein the flaky substrate is mica, kaolin, sericite, talc, silica or alumina.

3. The ultraviolet absorbent according to claim 1, wherein said zinc carbonate particles have a mean major diameter less than 350 nm and an aspect ratio of greater than 10.

4. The ultraviolet absorbent according to claim 1, wherein the complex forming agent is selected from the group consisting of: citric acid, oxalic acid, phthalic acid, maleic acid, tartaric acid, and ethylenediamine-tetracetic acid.

5. The ultraviolet absorbent of claim 1, comprising 30 to 250 parts by weight of zinc oxide based on 100 parts by weight of the substrate.

6. The ultraviolet absorbent of claim 5, comprising 50 to 150 parts by weight of zinc oxide based on 100 parts by weight of substrate.

7. The ultraviolet absorbent according to claim 2, wherein said flaky substrate has a mean particle size of 2.0 to 4.0 $\mu$m.

8. The ultraviolet absorbent of claim 1, wherein said ultra-fine zinc oxide particles are treated with an organic silicone compound.

9. A cosmetic material, coating composition, plastic or ink, comprising an ultraviolet absorbent of claim 1.

* * * * *